(12) United States Patent
Weil et al.

(10) Patent No.: US 9,176,071 B2
(45) Date of Patent: Nov. 3, 2015

(54) DEVICE, KIT AND METHOD FOR INSPECTION OF AN ARTICLE

(75) Inventors: Romain Weil, Chatuzange (FR); Patrick Prochaska, David City, NE (US)

(73) Assignee: Becton Dickinson France, Le Pont de Claix (FR)

( * ) Notice: Subject to any disclaimer, the term of this patent is extended or adjusted under 35 U.S.C. 154(b) by 462 days.

(21) Appl. No.: 13/643,201

(22) PCT Filed: Apr. 22, 2011

(86) PCT No.: PCT/EP2011/056500
§ 371 (c)(1),
(2), (4) Date: Nov. 20, 2012

(87) PCT Pub. No.: WO2011/134914
PCT Pub. Date: Nov. 3, 2011

(65) Prior Publication Data
US 2013/0057677 A1 Mar. 7, 2013

(30) Foreign Application Priority Data
Apr. 26, 2010 (EP) ..................................... 10305438

(51) Int. Cl.
*G01N 21/90* (2006.01)
(52) U.S. Cl.
CPC ............ *G01N 21/9081* (2013.01); *G01N 21/90* (2013.01)
(58) Field of Classification Search
CPC ........................ G01N 21/88; G01N 2033/0081
USPC ......... 348/125–131; 356/237.1, 237.2, 237.3, 356/239.1, 239.2, 240.1
See application file for complete search history.

(56) References Cited

U.S. PATENT DOCUMENTS

| | | | | |
|---|---|---|---|---|
| 4,606,635 A | * | 8/1986 | Miyazawa et al. | 356/240.1 |
| 4,697,076 A | * | 9/1987 | Yoshida | 250/223 B |
| 4,924,083 A | | 5/1990 | Ishikawa et al. | |
| 5,268,735 A | * | 12/1993 | Hayashi | 356/239.1 |
| 5,400,135 A | * | 3/1995 | Maeda | 356/239.1 |
| 5,615,007 A | * | 3/1997 | Matsuura et al. | 356/237.1 |
| 7,292,330 B2 | * | 11/2007 | Saunders et al. | 356/237.2 |
| 7,528,942 B2 | * | 5/2009 | Nakano et al. | 356/237.3 |
| 8,161,810 B2 | * | 4/2012 | Cadieux et al. | 73/149 |

(Continued)

FOREIGN PATENT DOCUMENTS

| | | |
|---|---|---|
| GB | 881765 | 11/1961 |
| JP | 5444587 A | 4/1979 |

(Continued)

*Primary Examiner* — Paulos M Natnael
(74) *Attorney, Agent, or Firm* — The Webb Law Firm (57) ABSTRACT

The invention relates to a device for inspecting the surface of an article having an edge with an end face, said device including:
a support for supporting said article,
a light source capable of emitting a light in a direction D, and
a filter for stopping part of the light of said light source which is emitted or diffused out of direction D,
said filter being provided with a hole intended to receive said article when said article is provided on said support, said support being positioned with respect to said light source and said filter so that, when said article is provided on said support, the end face of said edge is substantially perpendicular to said direction D. The invention also relates to a kit comprising such a device and to a method for inspecting the surface of the article.

18 Claims, 4 Drawing Sheets

(56) References Cited

U.S. PATENT DOCUMENTS

| | | | |
|---|---|---|---|
| 2002/0162979 A1* | 11/2002 | Kusunose | 250/559.45 |
| 2003/0189703 A1* | 10/2003 | Yonezawa et al. | 356/237.2 |
| 2004/0000652 A1* | 1/2004 | Guha et al. | 250/559.45 |
| 2010/0097451 A1 | 4/2010 | Bruce et al. | |
| 2010/0231902 A1* | 9/2010 | Markwort et al. | 356/237.2 |

FOREIGN PATENT DOCUMENTS

| | | |
|---|---|---|
| JP | 6186173 A | 7/1994 |
| WO | 2008051576 A2 | 5/2008 |

* cited by examiner

DEVICE, KIT AND METHOD FOR INSPECTION OF AN ARTICLE

The present invention relates to a device for inspecting an article, such as for example a drug container. The present invention also relates to a kit comprising such a device and an article to be inspected. The invention further relates to a method for inspecting a surface of an article, such as a syringe.

Many medical containers are made of transparent or clear materials such as glass and plastic. It is desirable that these containers or articles have as few defects as possible, either at a surface or in a wall of the article, for example in the thickness of a wall in the case of a medical article such as a container. The terms "article," "medical article" and "medical container" are used interchangeable herein.

U.S. Pat. No. 5,615,007 describes a method for inspecting the flange of a syringe in order to detect whether the flange comprises a chip or a crack. The method described in this document consists in illuminating the side of the flange with a light and carrying out an image processing based on an image signal reflected by the edge of the flange, by means of a camera located in an upward slant direction. An irregular state of the image signal caused by the reflected light indicates the presence of a chip or of a crack in the flange.

In addition to chips and cracks, such as described in U.S. Pat. No. 5,615,007, an article may also contain defect on a surface or within a wall. While such defects may not impact the strength of the article, they may still be undesirable. For example, a defect on a surface or within a wall of a medical container may make it difficult to inspect the contents of the container, or to determine if the container is homogeneously coated, for example with a layer of silicone in order to allow a better emptying of the article. A defect on a surface or within a wall of a medical container may be difficult to distinguish, upon visual inspection, from material provided or contained within the container such as, for example a medicament contained within the container, or a lubricant provided on an inner surface of the container.

Such cosmetic defects may not be present only on the flange of the medical article, in the case where the medical article is a syringe, but everywhere on the surface of the various walls forming the article, for example on the outer and/or the inner surfaces of the barrel in the case of a syringe.

Nevertheless, if these defects are too numerous and/or too important in size, they hinder the visual inspection directed toward the contents of the article, where such inspection is a critical step in the quality validation process for the medical article.

For example, pharmaceutical companies inspect the syringes once they are filled with a medicine, in order to determine whether any undesired particulate matter is present in the liquid substance contained in the syringe. For instance, such controls aim at rejecting the prefilled syringes in which the medicine, usually under the form of a liquid substance, would contain aggregates or foreign particles. Indeed such aggregates or foreign particles would be likely to get stuck in the tip of the syringe at the time of injection, rendering the injection step dangerous and/or incorrect. Alternatively, such particulate matter may be injected into the patient, which is also an undesirable and potentially dangerous situation. The problem is that such controls, which may be performed by taking pictures analyzed with computers, do not distinguish the aggregates present in the liquid medicine, which are likely to jeopardize the injection, from simple cosmetic defects contained on a surface or within a wall of the syringe, which have no impact on the quality or safety of injection of the liquid substance.

As a result, and in order to be on the safe side, the pharmaceutical companies may reject some filled syringes that would yet be adequate for a proper injection, but that present cosmetic defects that are not distinguishable from potential aggregates by a typical visual inspection. Such a procedure leads to a significant waste of medicine and is very costly for the pharmaceutical companies.

The method described in U.S. Pat. No. 5,615,007 mentioned above is not appropriate for determining the quantity and the sizes of the cosmetic defects on the entire inner and/or outer surfaces of the walls forming a medical article. Indeed, such a method, by simply illuminating the flange without setting any particular conditions regarding the environment of the tested article and capturing the light reflected by the edge of the flange, does not allow an efficient inspection of the rest of the article.

It is thus desirable to be able to determine various information regarding certain defects potentially present on a surface or within a wall of a medical article. For example, it may be desirable to determine the number or quantity of defects, their size, their dimensions, in particular length and width, and this, on an entire inner and/or outer surface of a wall of an article.

It is thus also desirable to provide a device and a method for allowing a quick and reliable inspection of certain defects on substantially the entire surface of an article, such as syringes, vials, cartridges, etc., in order to determine if such an article contains certain defects that may render the article unsuitable for use.

The present invention is directed to a device for inspecting an article that enables easy and rapid inspection of a surface of an article. A device in accordance with an embodiment of the present invention may be used to detect defects on a surface or within a wall of an article such as, for example, by way of illustration and not limitation, a light conducting tubular article such as a glass syringe.

A first aspect of the present invention is a device for detecting a defect in or on a wall of an article having at least one end provided with an edge having an end face, said device including at least:

a support intended to support said article, a light source capable of emitting a light at least in a direction D, and a filter positioned with respect to said light source so as to stop at least part of the light of said light source which is emitted or diffused out of said direction D, said filter being provided with at least a hole intended to receive said article when said article is provided on said support, wherein said support is positioned with respect to said light source and said filter so that, when said article is provided on said support, the end face of said edge is substantially perpendicular to said direction D.

In accordance with embodiments of the present invention, and as will appear from the description below, the surface of an article may be quickly and easily inspected for cosmetic defects, by a device and process that includes simply causing light to be conducted by and through the article.

Indeed, the device of the invention allows having a better concentration of the light in the wall of the article to be inspected and therefore a better contrast at the location of the cosmetic defects. In particular, the device of the invention allows avoiding the interference of the direct light emitted by the light source, therefore rendering the visual inspection more efficient.

In the device of the invention, the end face of the edge is substantially perpendicular to the direction D, in other words the end face of the edge faces the direction D, so as to directly receive the light emitted in said direction D from the light source.

In embodiments, said filter is positioned with respect to said light source and to said article so as to substantially stop the light of said light source which is emitted or diffused in direction of the part of the article not comprising the edge, when said article is provided on said support. For example, said filter comprises an enclosure substantially surrounding said light source and said edge, the part of the article not comprising said edge extending out of said enclosure via said hole, when said article is provided on said support, said enclosure being made of a material capable of preventing the passage of light.

Because of the specific structure of the device of the invention, the ratio between the light emitted from the light source, or diffused, in direction of the end face of the edge of the article when the article is installed on the support, and the light emitted by the light source, or diffused, in all the other directions, is increased with respect to a device as described in the prior art, like the device described in U.S. Pat. No. 5,615,007. As a consequence, a higher amount of light, either directly emitted by the light source or diffused, is caused to enter the edge of the article and is conducted through the thickness of the edge and through the thickness of the light conducting material forming the wall of the article, and is thus also conducted on the entire length and width of the wall and in an uniform way. In addition, a very small amount of light, tending to substantially no light at all, either directly emitted by the light source or diffused, is directed towards the rest of the article, in other words towards the part of the article not comprising the edge. Consequently, the visualization of the part of the article other than the edge is therefore neither polluted nor hindered by the undesired surrounding presence of light.

As a result, while the light which has entered the edge travels through the light conducting material, each time the light encounters a modified refractive index, corresponding to a defect and/or a relief on the surface of the wall, either on its outer surface or on its inner surface, the light concentrates on the defect and/or relief and generates a visible contrast in intensity of light which materializes the defect and/or relief for the eye of the observer and/or a camera.

In accordance with embodiments of the present invention, the characterization of the defect and/or relief is immediate, very simple and easy, and can be made by simply visually evaluating the illuminated article, without the need of sophisticated measuring devices. By simply observation, it can be determined whether an article should be kept or rejected. Of course, a camera and computer devices may be also used for completing the inspection step and for making the decision as to whether keep or reject an article.

In embodiments of the present invention, the light source is capable of emitting a multidirectional light. Such an embodiment allows the light entering the edge to diffuse within the thickness of the wall forming the article in all directions: when the article is a tubular article, such an embodiment permits a visualization of the cosmetic defects on a wide angle of the circumference of the wall forming the tubular article, inside and outside.

As used herein, the term "tubular article" refers to an article having the shape of a tube or of a barrel with two opposite ends, for example a proximal end and a distal end. The ends of the tubular article may each be open or closed. For instance, when the tubular article is a syringe, its distal end may be substantially closed except for a channel for receiving a needle cannula or for providing a fluid path for a substance contained in the syringe to be expelled, and its proximal end may be open and closable by a plunger. When the tubular article is a cartridge or a vial, its distal end may be closed and its opposite or proximal end may be sealed or sealable by, for example, a stopper or closure means. In embodiments, the article is a tubular article.

In the present application, the distal end of an article is to be understood as meaning the end furthest from the user's hand and the proximal end is to be understood as meaning the end closest to the user's hand when the article is in use. Likewise, in this application, the "distal direction" is to be understood as meaning the direction of injection or towards a patient, and the "proximal direction" is to be understood as meaning the opposite direction to the direction of injection or away from a patient.

In an alternative embodiment, the light source is capable of emitting a unidirectional light, like a LASER (light amplification by stimulated emission of radiation).

In embodiments, the light source is selected from the group comprising a light emitting diode (LED), a discharge lamp, an incandescent lamp and combinations thereof. Other suitable light sources are also contemplated by, and within the scope and spirint of the present invention.

In embodiments of the present invention, the support is mainly a two-dimensional element, such as a plate or an O ring, defining a plane P. For example, the support is a two-dimensional element, like a plate, a plaque, a sheet, or a ring, upon which the article may rest, or alternatively, the support may be an open ring, acting like jaws capable of moving within a plane P and of grasping the article. The support generally defines a plane P that may be oriented transverse to a longitudinal axis of the article. For example, when the tubular article is a syringe or a vial, the outer flange of the syringe, or the collar of the mouth of the vial may rest on the plate which is maintained horizontally. In another embodiment, said support is an O ring, and a part of the syringe, cartridge or vial may bear on the O ring.

The light source may be substantially located in the plane P such that the light source is essentially located in the plane P defined by the support; provided that the point from which the light is emitted is located in the plane P, so that at least part of the light emitted from the light source in the direction of the support has a light path that is contained within the plane and that is parallel to the support, said light path being therefore substantially aligned on direction D.

In embodiments of the present invention, the inventive device may further comprise a rod extending from said support in a direction B perpendicular to said plane P, the rod passing through the hole of the filter and being intended to at least partially support the article: for example, when the article is a tubular article, the rod is intended to be received within the tubular article when the article is located on the support. As will appear from the description below, a rod or similar structure provides a background for visualizing only the defects present on the front part of the tubular article, and blocks the back part of the tubular article from the view. Thus, the present invention enables detection of defects on a specific surface of a specific wall of an article.

In embodiments of the present invention, the inventive device further comprises a motor for automatically rotating the support around an axis of revolution of said support: this axis of revolution is preferably coaxial with the longitudinal axis A of the article, when the article is mounted on the support. As will appear from the below description, such an embodiment allows rotating easily a tubular article to be inspected, so as to complete an efficient inspection of the whole circumference of the surface of the tubular article.

In embodiments, the light source is distributed along an outer periphery of the support. Such a distribution of the light source allows obtaining a wide diffusion of the light entering the edge and the article and therefore a uniform illumination of the article on its entire circumference. For example, the light source may comprise a plurality of LEDs distributed along the outer periphery of the support. In embodiments, the support is a circular plate. Alternatively, the light source may be distributed along one or several parallel lines located on opposite sides of the support.

The filter of the device of the invention is intended to stop at least part of the light of the light source which is emitted or diffused out of the direction D, in particular in the direction of the part of the article not comprising the edge. The filter of the device of the invention may thus be made of any non-transparent material capable of substantially preventing the passage of light. In embodiments, the filter comprises an enclosure substantially surrounding the support, except for the hole, the enclosure being made of a material selected from plastic materials, metallic materials and combinations thereof.

Another aspect of the present invention is a kit comprising a device as described above and a light conducting article having at least one end provided with an edge having an end face. As used herein, the term "light conducting article" refers to an article capable of having light transmitted therethrough.

Said light conducting material may be selected from the group comprising glass, polyurethane, polyethylene, and combinations thereof. In embodiments, said light conducting article is made of glass.

In embodiments, said article is mounted on said support, the end face of said edge being substantially perpendicular to said direction D.

In embodiments, said article is tubular and may be selected from the group comprising a syringe body, a vial, a cannula, a catheter.

Another aspect of the present invention is a kit comprising a device as described above and a camera for capturing an image of the illuminated article. The kit may also include a computer for processing said image of the article and for producing a pictorial representation of said image. For example, software may be used in combination with the computer, to analyze the image and to determine the geometry of the defects and/or the cumulative area occupied by the defects. For example, a limit value of the cumulative area occupied may be determined above which the article is rejected and be disposed of.

In embodiments, the article may be prefilled with a liquid substance, such as, for example, a liquid drug substance.

Another aspect of the invention is a method for inspecting the surface of a light conducting article having at least one end provided with an edge having an end face and made of a light conducting material, comprising the following steps:
    providing a device as described above,
    supporting said article on said support, said end face of said edge being perpendicular to said direction D, said article being received in said hole,
    illuminating said tubular article by means of said light source,
    inspecting the surface of the illuminated article.

Such a method allows detecting a defect in or on a wall of the article.

In embodiments, the inspecting step is conducted by human eye, in embodiments by human eye only.

Alternatively or in combination, the inspecting step may further comprise capturing an image of at least a portion of the surface of the illuminated article by means of a camera and treating said captured image by means of a computer so as to produce a pictorial image of said portion.

In embodiments, said article having a longitudinal axis A, said article is rotated around the longitudinal axis A of an angle selected in the range of 0-360° and said inspecting step is repeated. For example, said rotation and inspection are reproduced for a number of times necessary for obtaining a pictorial image of the whole surface of the article.

Such a method, thanks to the device of the invention, allows obtaining a rapid, easy overview of the presence and quantity of potential cosmetic defects on the surface of an article, for example a tubular article, in particular made of a transparent material, such as glass or plastic syringe. It is therefore possible to set up a limit value above which the inspected article should be rejected.

The device, kit and method of the invention will now be further described in reference to the following description and attached drawings in which.

Figure 1:
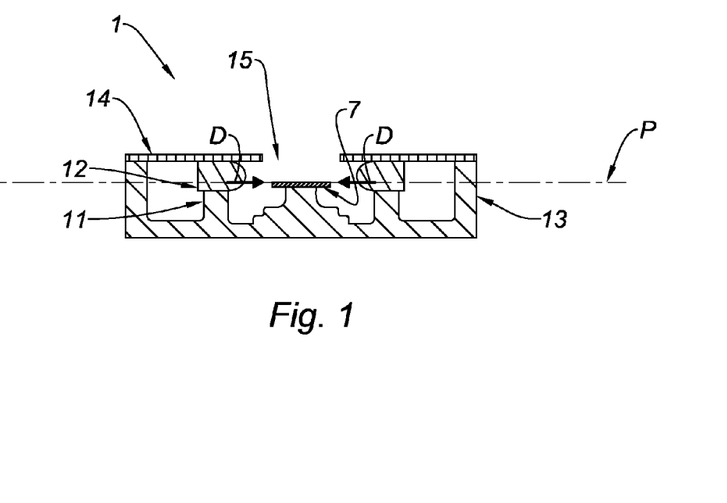
FIG. 1 is a cross-sectional view of a first embodiment of the device of the invention.
Figure 2:
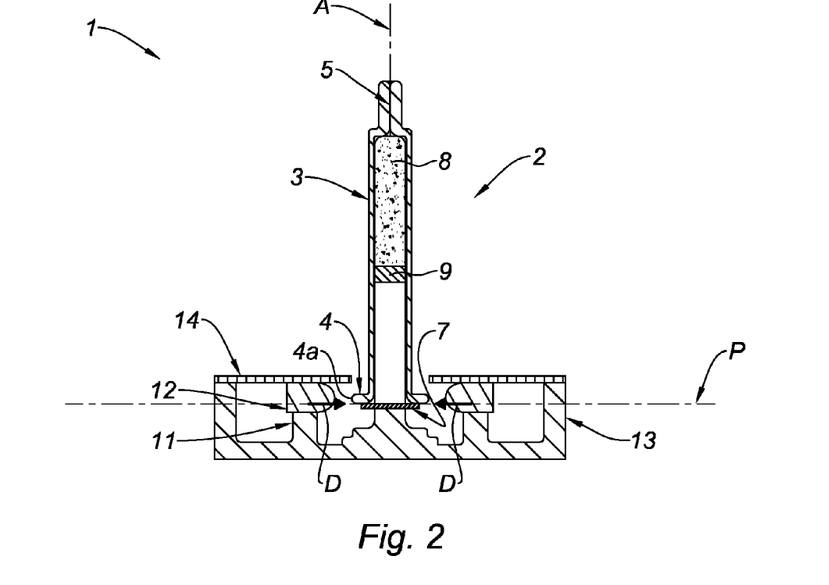
FIG. 2 is a cross-sectional view of the device of FIG. 1 with a prefilled syringe mounted on the device.
Figure 3A:
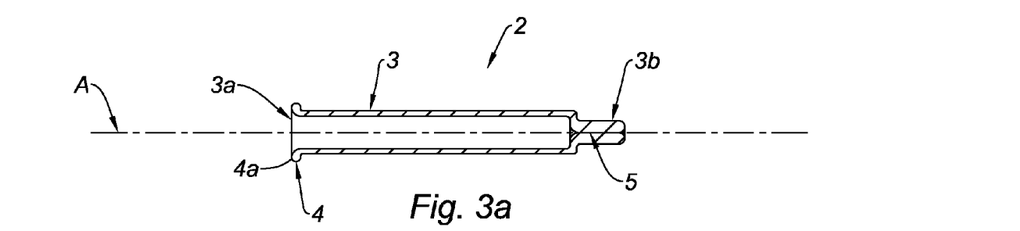
FIG. 3a is a cross-sectional view of a syringe body that can be assessed according to the method of the invention.
Figure 3B:
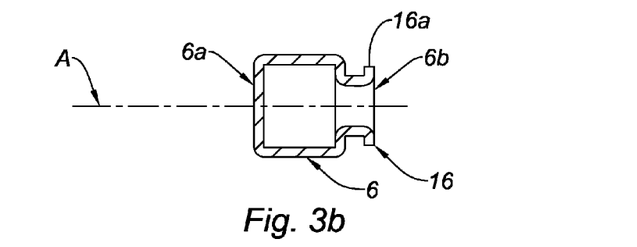
FIG. 3b is a cross-sectional view of a vial provided with a flange that can be assessed according to the method of the invention.

With reference to FIGS. 1 and 2 is shown a first embodiment of the device 1 according to the invention, usable for inspecting the surface of an article having an end provided with an outer flange, such as those shown on FIGS. 3a and 3b.

An exemplary article for use in connection with a device of the present invention is depicted in FIG. 3a: on this figure is shown a generally tubular article in the form of a syringe body 2 comprising a tubular barrel 3 having a longitudinal axis A, a proximal end 3a and a distal end 3b. The proximal end 3a of the barrel 3 is open and is provided with an edge under the form of an outer flange 4 providing bearing surfaces for the user at the time of injection. As appears from FIG. 3a, the outer flange 4 extends in a direction substantially perpendicular to the longitudinal axis A and has an end face 4a: as will appear from the following description, this end face 4a has a certain thickness providing for an entry for a light to travel within the thickness of the wall of the barrel 3. The distal end 3b of the barrel 3 is provided with a conic distal tip 5 providing a passage for the transfer of a medicine contained in the barrel 3 from the syringe 2 to the site of injection. The conic distal tip 5 is intended to receive a needle (not shown). As is generally known in the art, the needle may be fixed to the tip 5 (i.e., a staked needle), or the needle may be removably secured to the tip 5 (e.g., via a Luer-type connection).

The syringe body 2, as well as the barrel 3 and the outer flange 4, of FIG. 3a are made from a material, such as glass, or any other transparent material, such as polyurethane, polyethylene, and combinations thereof. In a preferred embodiment, the material from which the syringe body 2, the barrel 3 and the flange 4 are made is a light conducting material.

Moreover, on the example shown on FIG. 3a, the outer flange 4 and the barrel 3 are one single piece. Alternatively, the outer flange could be added on the barrel by any attaching means such as force fitting or snap-fitting.

Another exemplary article for use in connection with a device of the present invention is depicted in FIG. 3b. The article of FIG. 3b has a longitudinal axis A and has a generally tubular shape under the form of a vial 6. The vial 6 has a closed proximal end that is a generally flat bottom 6a, and an open distal end 6b under the form of a collar 16. The collar 16 extends in a direction substantially perpendicular to the longitudinal axis A and has an end face 16a. The end face 16a has a certain thickness providing for an entry for a light to travel within the thickness of the wall of the vial 6.

The vial 6 of FIG. 3b is made from a light conducting material such as glass or transparent plastic material.

Figure 8A:
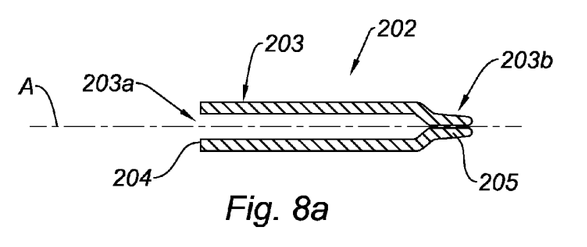
FIG. 8a is a cross-sectional view of a cartridge that can be assessed according to the method of the invention.
Figure 8B:
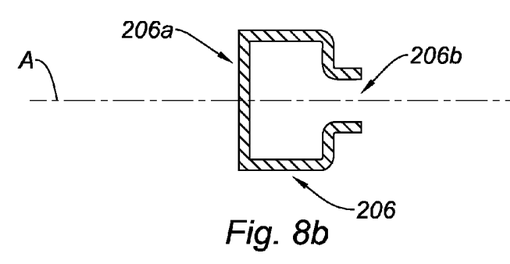
FIG. 8b is a cross-sectional view of a vial that can be assessed according to the method of the invention

Yet other articles suitable for use with the present invention are a cartridge or a vial without collar such as depicted in FIGS. 8a and 8b. In general, articles such as those depicted in FIGS. 3a, 3b 8a and 8b are generally known in the art.

With reference to FIGS. 1 and 2, a first embodiment of the device 1 of the invention is shown which is suitable for supporting a syringe body 2 (FIG. 3a) or a vial 6 (FIG. 3b).

The device 1 of FIG. 1 includes a support, under the form of a plate 7 on the example shown, for supporting a tubular article, such as a syringe body 2 as shown on FIG. 3a or a vial 6 of FIG. 3b. The plate 7 may be circular or any other shape suitable for supporting a desired article and is positioned on a horizontal plane P. The plate 7 is mainly two-dimensional and defines the plane P. The device 1 of FIGS. 1 and 2 further comprises a light source 11 comprising a plurality of light emitting diodes 12 on the example shown.

Alternatively or in combination, in embodiments not shown, the light source 11 may be selected from discharge lamps, incandescent lamps and combinations thereof. In the embodiment depicted in FIGS. 1 and 2, the plurality of light emitting diodes 12 is distributed along the outer periphery of the plate 7. As appears clearly from FIGS. 1 and 2, the light source (11, 12) is located in plane P, in alignment with the plate 7. Thus, when the article, here the syringe body 2, rests on the plate 7, as shown in FIG. 2, the light source (11, 12) is substantially aligned with the end face 4a of the outer flange 4 of the article.

Each light emitting diode 12 of the light source 11 is capable of emitting a light at least in a direction D, i.e., for each light emitting diode in the direction of the plate 7. Preferably, the light source is a multidirectional light source.

The device 1 of FIGS. 1 and 2 further comprises an enclosure 13 that defines a filter and that generally surrounds and encloses the plate 7. A hole 15 is defined in the enclosure 13, the function of which will be explained later. The filter defined by enclosure 13 is intended to stop at least part of the light of the light source (11, 12) from being emitted or diffused out of the direction D, and in particular out of plane P. In a preferred embodiment, the enclosure 13 is made of a non transparent material: the non transparent material may be selected from plastic materials, metallic materials and combinations thereof. For the embodiment of FIGS. 1 and 2, the enclosure 13 comprises a horizontal wall 14, located above the plate 7, the hole 15 being defined in the horizontal wall 14. Preferably, the hole 15 is sized and shaped so as to facilitate placement of the article, here the syringe body 2, on the plate and removal therefrom.

In FIG. 2 is shown the device 1 of FIG. 1 with a syringe 2 prefilled with a medicinal product 8 and mounted on the device 1. The syringe 2 includes a stopper 9 in the syringe barrel 3 so as to securely close the proximal end of the barrel 3. Alternatively, an empty syringe could be mounted on the device 1.

In the example shown on FIG. 2, a surface of the outer flange 4 of the syringe 2 rests on the plate 7, and the barrel 3 has been passed through the hole 15 of the wall 14. Alternatively, the syringe 2 could be replaced by a vial 6 of FIG. 3b: in such a case, the collar 16 of the vial 6 would rest on the plate 7, the body of the vial 6 passing through the hole 15.

As appears from FIG. 2, because of the specific structure of the device 1 of the invention, once the syringe 2 rests on the plate 7, the outer flange 4 of the syringe 2 is disposed in the plane P and is in alignment with the light source 11 and the light emitting diodes 12. As a consequence, the end face 4a of the outer flange 4 is perpendicular to the direction D which is the direction in which the light from the light emitting diodes is emitted: in particular, the thickness of the end face 4a directly faces the light emitted in direction D. As appears also from this FIG. 2, when the syringe 2 is provided on the plate 7, the enclosure 13 surrounds the light source 11 and the outer flange 4 provided with the end face 4a, while at the same time the part of the syringe 2 not comprising the outer flange 4, in other words the barrel 3, extends out of the enclosure 13, via the hole 15.

As a consequence, when the light source 11 is switched on, the light emitted in direction of the plate 7 is also emitted in the direction of the outer flange 4: this light, either directly emitted by the light emitting diodes 12 or diffused, follows a light path generally parallel or co-planar with the plane P and consequently encounters the end face 4a of the outer flange 4 and is conducted in and through the walls of the barrel 3 of the syringe 2, or generally, in and through the walls of the article.

At the same time, the enclosure 13 prevents light from the light source 11 from escaping from the enclosure 13. Specifically, wall 14 of the enclosure 13 stops the light emitted or diffused in the direction of the barrel 3. This ensures that light observed in the wall of the article is being transmitted in and through the wall, and is not light directed onto a surface of the article. Thus, embodiments of the present invention as disclosed herein reduce the undesirable effect of light illuminating the article from a source other than light transmitted in and through the wall of the article, i.e., reducing the effect of light illuminating the article by exposure on a surface of the article.

As explained above, the consequence is that on one hand, a higher amount of light, either directly emitted by the light source (11, 12) or diffused, is caused to enter the outer flange 4 of the syringe 2 and is conducted through the thickness of the light conducting material forming the outer flange 4 and the wall of the barrel 3 of the syringe 2; and, on the other hand, a smaller amount of light, either directly emitted by the light source (11, 12) or diffused, is directed towards the barrel 3 via the surrounding atmosphere: the visualization of barrel 3 is therefore neither polluted nor hindered by the undesired presence of light diffused or directed in the environment of the barrel 3.

The embodiment of the device of the invention shown on FIGS. 1 and 2 can be used for quick and easy characterization of cosmetic defects on the surface (inner and outer) of the syringe 2, i.e. on the surface of both the outer flange 4 and of the barrel 3, either by simple human eye observation or by use of a camera.

Indeed, while the syringe 2 is illuminated as described above, the light which has entered the outer flange 4 via the thickness of the end face 4a travels through the light conducting material forming the wall of the barrel 3: each time the light encounters a modified refractive index, corresponding to a defect and/or a relief on the surface of the wall of the barrel 3, either on its outer surface or on its inner surface, the light concentrates on the defect and/or relief and generates a visible contrast in intensity of light which materializes the defect and/or relief for the eye of the observer.

Because the atmosphere surrounding the barrel 3 is not polluted by undesired emitted or diffused light, the characterization of the defect and/or relief is immediate, very simple and easy for the human eye. The observer can readily decide whether an article may be kept or on the contrary rejected. Of course, alternatively, a camera and computer devices may be also used for completing this inspection step.

FIGS. 4 to 7 depict a second embodiment of the device of the invention, particularly suitable for inspecting an empty article such as a syringe body, such as the one described on FIG. 3a.

Figure 4:
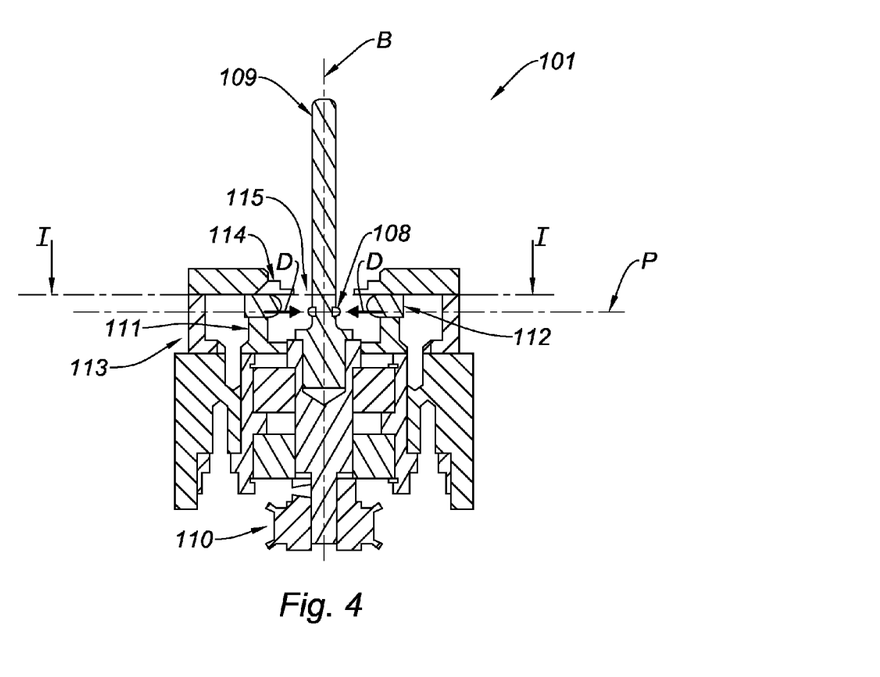
FIG. 4 is a cross-sectional view of a second embodiment of the device of the invention.
Figure 5:
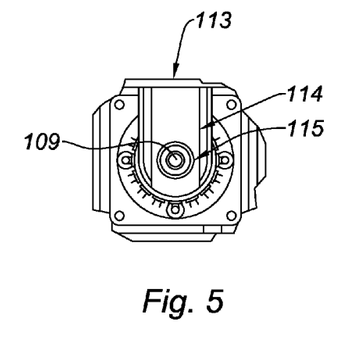
FIG. 5 is a top view of the device of FIG. 4.

The device 101 of FIG. 4 includes a support, under the form of an O-ring 108 on the example shown, for supporting a tubular article, such as a syringe body 2. The O-ring 108 may be made of rubber for example and is positioned on a horizontal plane P. The O-ring is mainly two-dimensional and defines said plane P.

In the embodiment of FIGS. 4 to 7, the device 101 further comprises a rod 109 extending through a center of the O-ring 108, along an axis B generally perpendicular to the plane P and generally parallel or co-planar with the longitudinal axis A of the syringe 2 when the syringe 2 is mounted on the O-ring.

The device 101 of FIGS. 4 to 7 further comprises a motor 110 for automatically rotating the O-ring 108 and the rod 109 around the axis B.

Figure 6:
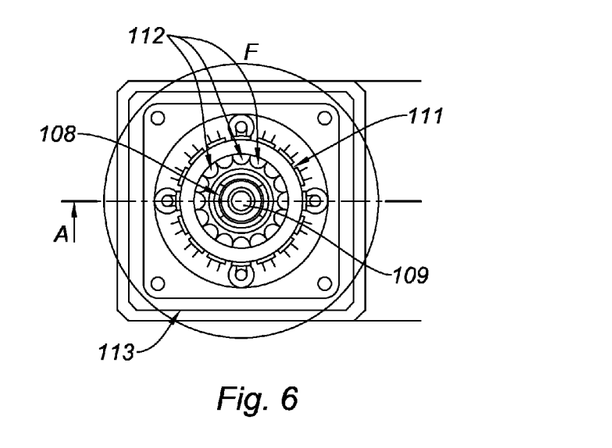
FIG. 6 is a cross-sectional view of the device of FIG. 4 taken along line I-I.

Like the embodiment of FIGS. 1 and 2, the device 101 of FIGS. 4 to 7 further comprises a light source 111 comprised of a plurality of light emitting diodes 112 on the example shown. The plurality of light emitting diodes 112 is distributed generally along the outer periphery of O-ring 108, as shown in FIG. 6. This distribution of diodes 112 may also be used for the embodiment of FIGS. 1 and 2. In accordance with a preferred embodiment shown in FIG. 6, the light source 111 comprises sixteen light emitting diodes 112 regularly distributed along the circumference of the O-ring 108.

Alternatively or in combination, in embodiments not shown, the light source may be selected from discharge lamps, incandescent lamps and combinations thereof.

As appears clearly from FIG. 4, the light source (111, 112) is located in plane P, in alignment with the O-ring 108. When the syringe 2 rests upon the rod 109 (see FIG. 7), the light source (111, 112) is in substantial alignment of the outer flange 4 of the syringe 2.

Each light emitting diode 112 of the light source 111 is capable of emitting a light at least in a direction D which is the direction of the O-ring 108, and more preferably a multidirectional light. In the embodiment shown, since the light emitting diodes are distributed along the circumference of the O-ring 108, the direction D is the radial direction. As a consequence, the end face 4a of the outer flange 4 is perpendicular to the direction D which is the direction in which the light from the light emitting diodes is emitted.

Figure 7:
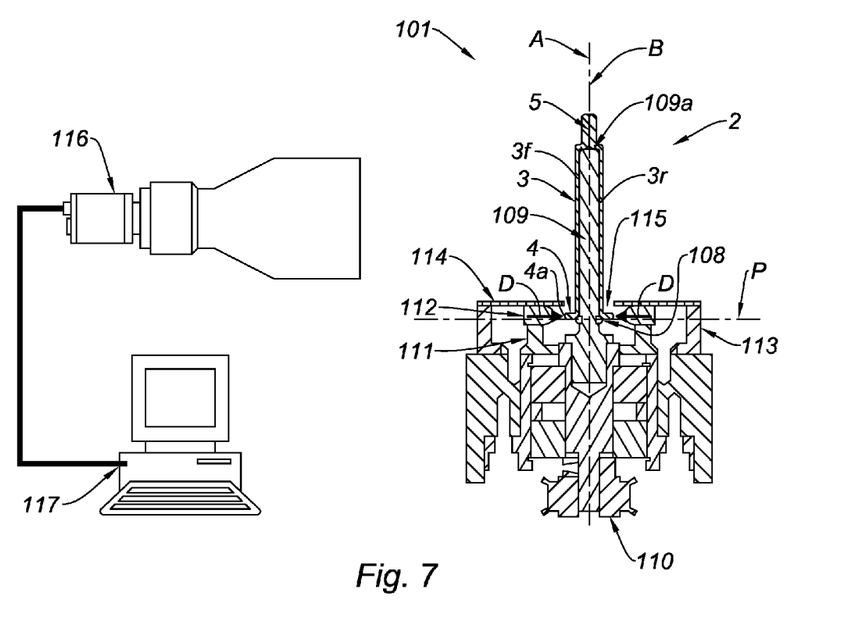
FIG. 7 is a cross-sectional view of a kit comprising the device of FIG. 4 once the syringe body of FIG. 3a is mounted on the device and illuminated, a camera and a computer.

Moreover, because of the regularly distribution of the sixteen light emitting diodes 112 as shown on FIG. 6, the light emitted and diffused in the direction D of the O-ring 108, and thus in the direction of the outer flange 4 once the syringe 2 is mounted on the O-ring as shown on FIG. 7, will be transmitted and diffused throughout the thickness of the entire wall of the barrel 3 of the syringe 2, in a uniform manner in all directions and on the whole circumference of the barrel 3.

The device 101 of FIGS. 4 to 7 further comprises a filter under the form of an enclosure 113, similar to that of the embodiment of FIGS. 1 and 2, substantially surrounding the O-ring 108, and provided with a wall 114 having a hole 115 facing the O-ring 108. The enclosure 113 is made of a non transparent material: the non transparent material may be selected from plastic materials, metallic materials and combinations thereof. As appears from FIG. 5, the hole 115 is circular and has a diameter allowing the rod 109 to pass through it. In an alternative embodiment not shown, the hole may have another shape, such as a square shape.

The method for inspecting the surface of a light conducting article with a device 101 of the invention of FIGS. 4-7, will now be described with reference to FIG. 7, in a particular example where the article is a syringe body 2 made of glass, as shown on FIG. 3a, and provided with an outer flange 4 also made of glass.

As shown on FIG. 7, the article, here a syringe body 2, rests on the device 101 by means of the outer flange 4 encountering the O-ring 108. As appears from this Figure, the rod 109 is received within the barrel 3 of the syringe 2 and its distal tip 109a may or may not contact the distal conic tip 5 of the syringe body 2. Once the syringe body 2 is installed on the O-ring 108 of the device 101 of the invention, the longitudinal axis A of the syringe body 2 is aligned with axis B. In this position, the enclosure 113 surrounds the light source 111 and the outer flange 4 provided with the end face 4a, while at the same time the part of the syringe 2 not comprising the outer flange 4, in other words the barrel 3 of the syringe 2 extends outside the enclosure 113 through the hole 115 of wall 114 of the enclosure 113.

To inspect the surface of the barrel 3 of the syringe body 2, the syringe body 2 is illuminated by the light source 111, i.e. the plurality of LEDs 112 distributed along the periphery of the O-ring 108. As seen above, the light source 111 is located in the alignment of the O-ring 108, and thus in the alignment of the outer flange 4 of the syringe 2. The emitted light follows direction D and enters the thickness of the end face 4a of the outer flange 4. As explained above with reference to the description of FIGS. 1 and 2, the outer flange 4 acts as guiding means for conducting the light emitted and diffused from the light 111 source in the direction of the outer flange 4 in and through the thickness of the wall of the barrel 3 of the syringe body 2, and the enclosure 113 acts as filtering means for stopping the light emitted and diffused from the light 111 source in the direction of the barrel 3 from polluting the surrounding atmosphere of the barrel 3.

As seen above, while the syringe 2 is illuminated as described above, the light which has entered the outer flange 4 via the end face 4a travels in and through the light conducting material forming the wall of the barrel 3: each time the light encounters a modified refractive index, corresponding to a defect and/or a relief on the surface of the wall of the barrel 3, either on its outer surface or on its inner surface, the light concentrates on the defect and/or relief and generates a visible contrast in intensity of light which materializes the defect and/or relief for the eye of the observer or for a camera 116.

The characterization of the defect and/or relief is immediate, very simple and easy for the human eye. The characterization and quantitative and qualitative measures of the defects and/or reliefs may also be completing with the help of a camera coupled to a computer 117.

As shown on FIG. 7, the device/kit of the invention may further comprise a camera 116 for capturing an image of the illuminated syringe 2 and a computer 117 for treating the captured image so as to produce a flattened image. The flattened image reproduces the presence of the defects and/or reliefs which appear as a concentration of light, as explained above. The camera 116 is set up so as to capture an image corresponding to only an angular portion of the circumference of the barrel 3, so that the curvature of the barrel 3 does not interfere with the quality of the data collected on the image. Thus, the motor 110 causes the article, here the syringe body 2, to rotate in increments small enough so as to represent a substantially planar section of the article, thus substantially removing curvature from the section of the article evaluated by the device of the present invention.

In the embodiment of the device of the invention described in FIGS. 4-7, the rod 109 also constitutes a background for the part of the barrel 3 located between the rod 109 and the camera 116 as shown on FIG. 7, herein after called the front part 3f of the barrel 3. Thanks to the presence of the rod 109, the state of the surface of the part of the barrel 3 located behind the rod 109, hereinafter called the rear part 3r of the barrel 3, does not interfere with the state of the surface of the front part 3f.

In embodiments, like the one of FIGS. 1 and 2, the rod 109 is removed. In such a case, the eye or the camera captures an image of the surfaces of both the front and the back parts of the barrel at the same time.

In order to inspect the entire circumference of the surface of the barrel 3, the article, i.e. the syringe body 2, is rotated around the longitudinal axis A of an angle selected in the range of 0-360° thanks to the motor 110 and the inspecting step is repeated. This step may be reproduced for a number of times necessary for obtaining a flattened image of the whole surface of the article.

For example, the following steps may be completed: after a first inspection is completed, the article, the syringe body 2, is rotated for example by an angle of 3.6°. A second inspection is completed. This step is repeated for example 100 times. The method of the invention allows performing a series of at least 100 inspections for example, all around the circumference of the barrel 3 of the syringe 2, thereby enabling to obtain a map of the cosmetic defects and/or reliefs on the whole surface, inner and outer, of the barrel 3. The method of the invention is therefore reproducible and can be used in an industrial process in order to determine whether the syringe bodies of a batch just manufactured are likely be suitable for further use for pharmaceutical companies or if they should be rejected and/or disposed of.

For example, it is possible to determine a maximum limit value of accumulated area for the cosmetic defects, above which it is decided that the syringe body is not suitable for use as a prefilled syringe, therefore justifying that the syringe body be disposed of. It is then possible to implement the method of the invention at an industrial process level in order to maintain only the syringe bodies satisfying to an accumulated area value, measured according to the method of the invention, below the maximum limit value.

Figure 9:
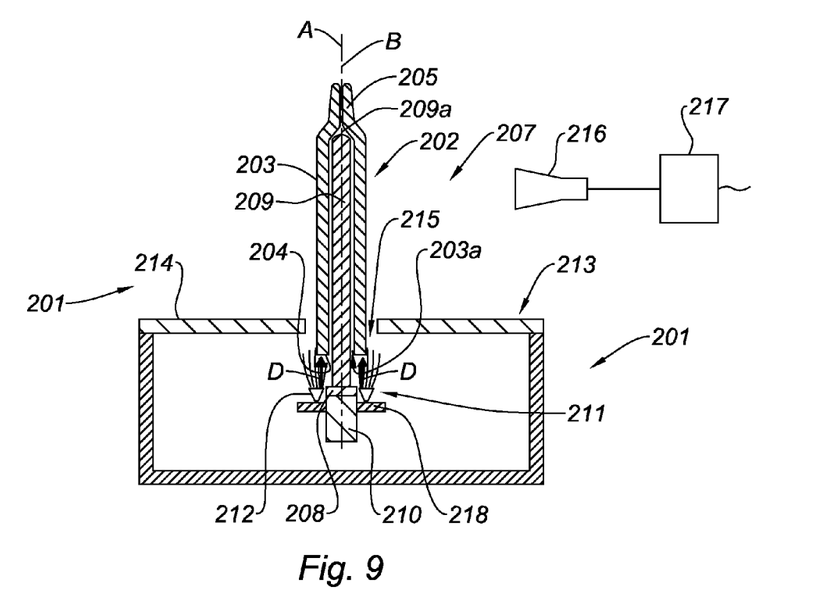
FIG. 9 is a cross sectional view of another embodiment of the device of the invention once the cartridge of FIG. 8a is mounted on said device and illuminated.

FIGS. 8a, 8b and 9 depict a variant of the device of the invention and articles, like a cartridge, to be assessed with such device.

On FIG. 8a, is shown an article having a substantially tubular shape under the form of a syringe body 202 comprising a tubular barrel 203 having a longitudinal axis A, a proximal end 203a and a distal end 203b. The proximal end 203a of the barrel 203 is open and is free of flange: as a consequence, the proximal end 203a has a free edge the end face 204 of which is perpendicular to the longitudinal axis A. The distal end 203b of the barrel 203 is provided with a conic distal tip 205 providing a passage for the transfer of a medicine contained in the barrel 203 from the syringe 202 to the site of injection. The conic distal tip 205 is intended to receive a needle (not shown).

The syringe body 202, as well as the barrel 203, of FIG. 8a are made from a light conducting material, such as glass, or any other transparent material, such as polyurethane, polyethylene, and combinations thereof.

On FIG. 8b is shown another embodiment of an article suitable for being assessed with the device 1 of the invention. The article of FIG. 3b has a longitudinal axis A and has a substantially tubular shape under the form of a vial 206. The vial 206 has a closed proximal end under the form of flat bottom 206a, and an open distal end 206b having a free edge the end face of which is perpendicular to the longitudinal axis A.

The vial 206 of FIG. 8b is made from a light conducting material such as glass, or any other transparent material, such as polyurethane, polyethylene, and combinations thereof.

In embodiments not shown, the article may be a cannula or a catheter, open at both ends, with free edges the end faces of which are perpendicular to the longitudinal axis of said cannula or catheter.

With reference to FIG. 9, the embodiment of the device 201 of the invention shown is particularly suitable for supporting a syringe body 202 such as described at FIG. 8a.

The device 201 includes a support 207, comprising a plate 208 and a rod 209 on the example shown, for supporting an article, such as a syringe body 202 as shown on FIG. 8a. As appears from FIG. 9, on the example shown, the plate 208 is intended to be put on a horizontal plane and the rod 209 extends from the center of said plate 208, in a direction B perpendicular to the plane of the plate 208, i.e. vertically in the example shown. As appears from FIG. 9, this direction B corresponds to the longitudinal axis A of the article when said article is mounted on the support 207.

The plate may have any shape, such as a round, rectangular or square shape. In an alternative embodiment not shown, the plate and rod may be replaced by grasping jaws capable of holding the article in the direction B, for example by grasping a closed end of said article or alternatively by grasping a part of the wall of the article that need not be assessed.

The device 201 of FIG. 9 further comprises a motor 210 for automatically rotating said support 207 around said direction B: said direction B is also the revolution axis of the support 207. On the example shown, when the motor operates, the whole support 207, encompassing the plate 208 and the rod 209, rotates.

The device 201 of FIG. 9 further comprises a light source 211 under the form of a plurality of light emitting diodes 212, lying on a support member 218 on the example shown.

Alternatively or in combination, in embodiments not shown, the light source may be selected from LASERS, discharge lamps, incandescent lamps and combinations thereof. For example, the light source may be a LASER emitting a unidirectional light in the B direction.

On the example shown, the plurality of light emitting diodes 212 is distributed along the outer periphery of the plate 208. The light source is positioned substantially in the alignment of the direction B: each light emitting diode 212 is capable of emitting a light in a direction D which is parallel to direction B. As a consequence, once a tubular article to be assessed with the device 201 of the invention is mounted on the support of the device of the invention, with its longitudinal axis A aligned on said direction B, as shown on FIG. 9, the direction D of the emitted light is substantially perpendicular to the end face 204 of the edge of the article 202.

The device 201 of FIG. 9 further comprises an enclosure 213 defining a filter acting as directing means for directing the light emitted from the light source 211 substantially along said direction D only. The enclosure 213 of the device 201 of FIG. 9 surrounds substantially the light source 211 and the end face 204 and comprises a piece of wall 214 parallel to said plate 208, comprising a hole 215 allowing substantially only the light emitted towards said direction D by the light source 211 to pass therethrough, as shown on FIG. 9. As such, the enclosure 213 substantially stops the light of the light source 211 which is emitted or diffused in direction of the part of the syringe body 202 not comprising the end face 204, in other words in direction of the barrel 203. For clarity's sake, the hole 215 shown on FIG. 9 appears to be large but in reality, the wall 214 is close enough to the barrel 203 so as to stop the light emitted from the light source 211 and prevent this light from reaching the outer surface of the barrel 203. As appears from FIG. 9, the rod 209 and the part of the barrel 203 not comprising the end face 204 extend outside the enclosure 213 through the hole 215. for a tubular article such as the syringe body 202, the hole 215 has preferably a diameter greater than the cross section of the tubular article, so as to allow said tubular article to be received within said hole 215.

The filter of the device 201 of the invention is intended to stop the part of the light of the light source not directed towards the D direction. The filter of the device 201 of the invention may thus be made of any non transparent material capable of stopping light. In embodiments, the enclosure 213 forming the filter may be made of a material selected from plastic materials, metallic materials and combinations thereof.

The method for inspecting the surface of a light conducting tubular article with a device 201 of the invention, will now be described with reference to FIG. 9, in a particular example where the tubular article is a syringe body 202, as shown on FIG. 8a, made of glass.

As shown on FIG. 9, a tubular article, here a syringe body 202, is installed on the support 207 of the device 201. As appears from this figure, the syringe body 202 is installed on the rod 209, so that the distal conic tip 205 of the syringe body 202 rests on the free end 209a of the rod 209 and so that the open end 203a of the syringe body 202, and in particular the end face 204 of its free edge, faces the light source 211. Once the syringe body 202 is installed on the support 207 of the device 201 of the invention, the longitudinal axis A of the syringe body 202 is aligned with the direction B, and the end face 204 of the edge is substantially perpendicular to the direction D.

When one wants to inspect the surface of the barrel 203 syringe body 202, he illuminates the syringe body 202 by means of the light source 211, i.e. the plurality of LEDs 212 distributed along the periphery of the plate 208. The light source 211 is located in the alignment of the direction B and is axially spaced from the open end 203a of the syringe body 202, and as a consequence, it illuminates the syringe body 202 from its open end 203a, substantially in direction D only and in particular in the direction of the end face 204 of its free edge, and not from the lateral walls of said syringe body 202. The direction D of the emitted light is therefore substantially parallel to the longitudinal axis A of the illuminated article. In the example shown, the free edge of the open end 203a acts as guiding means for conducting the light emitted from the light source 211 through the thickness of the wall forming the barrel 203 of the syringe body 202.

As appears from FIG. 9, the light emitted from the light source 211 is guided through the wall of the tubular barrel 203 by means of the free edge of the open end 203a facing the light source.

As appears from FIG. 9, the hole 215 of the piece of wall 214 of the enclosure 213 allows only the light emitted towards substantially said direction D to pass therethrough, therefore acting as directing means for directing the light emitted from the light source 211 substantially along said direction D only. This allows having a better contrast of the illuminated barrel 203 of the syringe body 202.

As shown on FIG. 9, the device/kit of the invention may further comprise a camera 216 for capturing an image of the illuminated article and a computer 217 for treating said captured image so as to produce a flattened image. The flattened image reproduces the presence of the defects which appear as a concentration of light, as explained above. The camera 216 is set up so as to capture an image corresponding to only an angular portion of the circumference of the tubular barrel, so that the curvature of the barrel 203 does not interfere with the quality of the data collected on the image.

In this step, the rod 209 constitutes a background for the part of the barrel 203 located between said rod 209 and said camera 216 as shown on FIG. 9, herein after called the front part of the barrel. Thanks to the presence of the rod 209, the state of the surface of the part of the barrel 203 located behind the rod 209, hereinafter called the back part of the barrel 203, does not interfere with the state of the surface of the front part.

In embodiments, for example when the support includes grasping jaws for holding the tubular article in the direction D, the rod 209 may be removed. In such a case, the camera 216 captures an image of the surfaces of both the front and the back parts of the barrel at the same time.

Alternatively, the inspection of the surface of the barrel 203 of the syringe body 202 may be completed by the human eye only.

In order to inspect the entire circumference of the surface of the barrel 203, the syringe body 2 is rotated around the longitudinal axis A of an angle selected in the range of 0-360° thanks to the motor 210 and the inspecting step is repeated. This step may be reproduced for a number of times necessary for obtaining a flattened image of the whole surface of the tubular article.

For example, the following steps may be completed: after a first inspection is completed, the syringe body 202 is rotated for example by an angle of 3.6°. A second inspection is completed. This step is repeated for example 100 times. The method of the invention allows performing a series of at least 100 inspections for example, all around the circumference of the barrel 203 of the syringe 202, thereby enabling to obtain a map of the cosmetic defects and/or reliefs on the whole surface, inner and outer, of the barrel 203. The method of the invention is therefore reproducible and can be used in an industrial process in order to determine whether the syringe bodies of a batch just manufactured are likely be suitable for further use for pharmaceutical companies or if they should be rejected and/or disposed of.

For example, it is possible to determine a maximum limit value of accumulated area for the cosmetic defects, above which it is decided that the syringe body is not suitable for use as a prefilled syringe, therefore justifying that said syringe body be disposed of. It is then possible to implement the method of the invention at an industrial process level in order to maintain only the syringe bodies satisfying to an accumulated area value, measured according to the method of the invention, below said maximum limit value.

The device and the method of the invention therefore allow improving the manufacturing process of light conducting articles such as syringe bodies, vials catheters and cannulas in the medical field. As described above in reference with FIGS. 1 and 2, the method of invention described above may also be used with prefilled syringes.

The invention claimed is:

1. A device for detecting a defect in or on a wall of an article having at least one end provided with an edge having an end face, said device comprising:
   a support intended to support said article,
   a light source capable of emitting a light at least in a direction D, and
   a filter positioned with respect to said light source so as to stop at least part of the light of said light source which is emitted or diffused out of said direction D, said filter being provided with at least a hole intended to receive said article when said article is provided on said support,
   wherein said support is positioned with respect to said light source and said filter so that, when said article is provided on said support, the end face of said edge is substantially perpendicular to said direction D, and
   wherein said filter comprises an enclosure substantially surrounding said light source and said edge.

2. A device according to claim 1, wherein said filter is positioned with respect to said light source and to said article so as to substantially stop the light of said light source which is emitted or diffused in direction of the part of the article not comprising the edge, when said article is provided on said support.

3. A device according to claim 1, wherein the part of the article not comprising said edge extending out of said enclosure via said hole, when said article is provided on said support, said enclosure being made of a material capable of preventing the passage of light.

4. A device according to claim 1, wherein said light source is capable of emitting a multidirectional light.

5. A device according to claim 1, wherein the light source is selected from the group comprising, a light emitting diode (LED), a discharge lamp, an incandescent lamp, and combinations thereof.

6. A device according to claim 1, wherein said support is mainly a two-dimensional element, such as a plate or an O ring, defining a plane P.

7. A device according to claim 6, wherein said device further comprises a rod extending from said support in a direction B perpendicular to said plane P, said rod passing through said hole of said filter and being intended to at least partially support the article.

8. A device according to claim 6, wherein said device further comprises a motor for automatically rotating said support around an axis of revolution of said support.

9. A device according to claim 1, wherein said light source is distributed along an outer periphery of said support.

10. A device according to claim 9, wherein said light source comprises a plurality of LEDs distributed along the outer periphery of said support.

11. A device according to claim 1, wherein said support is a circular plate.

12. A device according to claim 1, wherein said filter comprises an enclosure substantially surrounding said support, except for said hole, said enclosure being made of a material selected from plastic materials, metallic materials and combinations thereof.

13. A kit comprising a device for detecting a defect in or on a wall of an article according to claim 1, a camera for capturing an image of the illuminated article, and a computer for processing said image of the article and for producing a pictorial representation of said image.

14. A method for inspecting the surface of a light conducting article having at least one end provided with an edge having an end face and made of a light conducting material, the method comprising the following steps:
   providing a device according to claim 1,
   supporting said article on said support, said end face of said edge being perpendicular to said direction D, said article being received in said hole,
   illuminating said article by means of said light source,
   inspecting the surface of the illuminated article.

15. A method according to claim 14, wherein said inspecting step is conducted by human eye.

16. A method according to claim 14, wherein the inspecting step further comprises capturing an image of at least a portion of the surface of the illuminated article by means of a camera and processing said captured image by means of a computer so as to produce a pictorial image of said portion.

17. A method according to claim 14, wherein said article has a longitudinal axis A, and wherein said article is rotated around the longitudinal axis A of an angle selected in the range of 0-360° and in that said inspecting step is repeated.

18. A method according to claim 17, wherein said rotation and inspection are reproduced for a number of times necessary for obtaining a pictorial image of the whole surface of the article.

* * * * *